United States Patent [19]

Bahar

[11] Patent Number: 5,380,647
[45] Date of Patent: Jan. 10, 1995

[54] SIMPLE TEST FOR DETECTING CARCINOEMBRYONIC ANTIGEN IN STOOL

[75] Inventor: Kamal Bahar, Tehran, Islamic Rep. of Iran

[73] Assignee: Farrokh Saidi, Baltimore, Md.

[21] Appl. No.: 53,024

[22] Filed: Apr. 26, 1993

Related U.S. Application Data

[63] Continuation-in-part of Ser. No. 830,669, Feb. 4, 1992, abandoned, which is a continuation-in-part of Ser. No. 698,393, May 10, 1991, abandoned, which is a continuation-in-part of Ser. No. 650,753, Feb. 5, 1991, abandoned.

[51] Int. Cl.$^6$ .................. G01N 33/574; G01N 33/53; G01N 1/18
[52] U.S. Cl. .................. 435/7.23; 435/7.21; 435/7.9; 435/7.92; 435/803; 435/961; 436/518; 436/64; 436/177; 436/178
[58] Field of Search .................. 435/7.23, 7.21, 7.9, 435/7.92, 803, 805, 961, 970; 436/518, 64, 174, 177, 178, 813

[56] References Cited

U.S. PATENT DOCUMENTS

| | | | |
|---|---|---|---|
| 4,299,815 | 11/1981 | Hanson et al. | 424/1 |
| 4,871,834 | 10/1989 | Matsuoka et al. | 435/240.27 |
| 4,921,789 | 5/1990 | Salom et al. | 435/240.27 |

FOREIGN PATENT DOCUMENTS 0225709  6/1987  European Pat. Off.

OTHER PUBLICATIONS

Gold et al., "Specific Carcinoembryonic Antigens of the Human Digestive System" The Journal of Experimental Medicine 122:467–481, 1965.
Henslee et al., "Identification and Characterization of New Antigenic Fragments Related to Carcinoembryonic Antigen in Adult Feces," Cancer Research 52:4175–4182, 1992.
Matsuoka, "Characterization of carcinoembryonic antigen-related...feces," JPN J Cancer Res., 81:514–519, 1990; English abstract in Biological Abstracts, vol. 90, No. 41744, 1990.
Ochi et al., "Production of Antibody for $a_1$-Acid Glycoprotein Using Carcinoembryonic Antigen and Normal Fecal Antigen," Cancer Letters 20:173–182, 1983.
Rogers et al., "CEA-Like Activity in Normal Colon Tissue," European Journal of Cancer 16:127–131, 1980.
Shimano et al., "Usefulness of Carcinoembryonic Antigen Measurement in Feces of Patients with Colorectal Cancer," Dis. Col. & Rect. 30:607–610, 1987.
Sugano et al., "Detection of Increased Fecal Carcinoembryonic Antigen and Its Characterization as a Membrane-bound Form in Colorectal... Gastrointestinal Disorders," Jpn J. Cancer Res. 80:1156–1160, 1989.
Stubbs et al., "Faecal carcinoembryonic antigen (CEA) in patients with Large bowel cancer," European Journal of Surgical Oncology 13:433–436, 1987.
Thompson et al., "The Carcinoembryonic Antigen Gene Family: Structure, Expression and Evolution," Tumor Biol 9:63–83, 1988.
Stubbs, R. S., et al., Gut, vol. 27, pp. 901–905, 1986, "Faecal carcinoembryonic antigen in colorectal cancer patients".
Whatman, Price List, Jan. 1, 1989.
Stites, D. P., et al., Basic and Clinical Immunology, 4th Edition, published 1982, Lange Medical.
Publications, Los ALtos, CA, USA, pp. 347–355.
Fisher Catalog, 1991, p. 735.

Primary Examiner—Toni R. Scheiner
Attorney, Agent, or Firm—Fish & Richardson

[57] ABSTRACT

A rapid, simple, sensitive and reliable method for detecting fecal carcinoembryonic antigens in stool, indicative of the presence of the colorectal cancer is described. The invention is based on the discovery that previous methods of removing coarse and gelatinous materials from a stool and liquid mixture resulted in removing a significant amount of total CEA and CEA-like substances. By not removing or destroying or altering molecules smaller than 500,000 MW, in the process of preparing the stool sample to be examined, a significant portion of CEA and CEA-like substances will remain in the filtered liquid for detection.

15 Claims, No Drawings

SIMPLE TEST FOR DETECTING CARCINOEMBRYONIC ANTIGEN IN STOOL

CROSS REFERENCE TO RELATED APPLICATIONS

This application is a continuation-in-part of application Ser. No. 07/830,669 filed Feb. 4, 1992, now abandoned, which is a continuation-in-part of application Ser. No. 07/698,393, filed May 10, 1991, now abandoned, which is a continuation-in-part of application Ser. No. 07/650,753, filed Feb. 5, 1991, now abandoned; all of the foregoing are hereby incorporated by reference.

BACKGROUND OF THE INVENTION

This invention relates to detection of colorectal cancer.

Serum CEA (carcinoembryonic antigen) has failed to serve as a reliable marker of large bowel tumors. Stool CEA would seem more appropriate in this respect, but no methods are currently available to detect and measure cancer specific CEA in feces. There exists the need for a rapid, simple, noninvasive yet sufficiently sensitive method of testing stool for CEA and CEA-like substances to serve as a screening test for cancer of the large bowel.

SUMMARY OF THE INVENTION

The invention is based in part on the following hypothesis.

1. Normal colon mucosa cells actively excrete/secrete CEA-like antigens into the lumen of the bowel; additional CEA-like substances entering proximally (bile, gastric juice, etc.).
2. Measuring the total amount of antigens present normally in feces, in a manner least affecting their physicochemical nature, establishes a baseline.
3. Cancer of the large bowel discharges at the glycocalyx level excess tumor-specific CEA into the bowel lumen, in addition to and presumably in greater amount than expressed in the normal state.
4. A significantly higher level of gross amount of CEA and all other CEA-like substances in feces, as compared to an established normal baseline, would suggest the possible presence of a large bowel tumor.

Accordingly, the invention features a method for detecting CEA and CEA-like antigens in a stool sample, by the steps of:

a) mixing a freshly obtained stool sample with an aqueous buffer to yield a liquid mixture;

b) filtering the liquid mixture to remove only coarse and gelatinous particles but not molecules smaller than 500,000 MW; and c) diluting the filtrate in a stepwise manner with an appropriate diluent to permit measurement of all CEA and CEA-like substances.

This invention is based on my discovery that previous attempts at detecting carcinoembryonic antigen(s) in stool were aimed at characterization and identification of specific antigens for colorectal cancer in a manner which actually removed a significant amount of total CEA and CEA-like antigens present in feces.

Conventional filtration processes in preparing stood for assay of CEA and CEA-like antigens entail the use of fine pore filter paper with particle retention size on the order of microns. However, most of the antigens to be measured exist as macromolecules. Additionally, the family of carcinoembryonic antigens, functioning in part as cell adhesion molecules, are cell-membrane anchored, such anchorage being cleaveable by specific phospholipase C. Accordingly, a majority of such antigens are trapped by fine pore filter paper, preventing their entry into the filtrate (see Sugano K. et al.: Jpn J. Cancer Res. 80 1156–1160. 1989). Using a filter paper of very large particle retention size had the unexpected result of liberating a large number CEA and CEA-like antigens into the filtrate. Any filtration medium which is effective in removing coarse and gelatinous particles only can be used. A filter having an average pore size equivalent to that of "#40 Whatman filter paper" is preferred (No. 40 Whatman Filter Paper, Catalogue No. 1440 125 of Fisons International Apparatus Catalogue of Bishop Meadow Road, Loughborough, Leiccstershire LE 11 ORG, England; not to be mistaken for Grade 40 Quantitative filter paper, catalogue number 1140 Y 125, of 8 $\mu$m particle retention size, as indicated in Whatman Price List of Jan. 1989).

The invention avoids a conventional step which has been to use acid treatment in an effort to precipitate unwanted proteins. It has been shown that perchloric acid treatment reduces by one half the total amount of measurable antigens in stool (Henslee et al. in Cancer Research 52, 4175–4182, 1992). No acid treatment is used in the proposed methodology, to avert possible precipitation of the antigens.

Heat treatment is another commonly used step to separate heat stable CEA from heat labile non-CEA proteins in feces (Stubbs et al: GUT 27, 901–905, 1986). Heat treatment is likewise avoided in the new method to recover all antigens regardless of their heat lability or stability.

Centrifugation as a conventional enrichment procedure is likewise specifically avoided, not in order to reduce the number of assay steps or the amount of equipment required to perform the extraction, but because centrifugation may well separate off macromolecules containing antigens and hence reduce the total amount of antigens available to be assayed.

The method preferably includes a step of diluting the filtered liquid mixture at least 100-fold v/v, prior to assaying for CEA and CEA-like antigens. The reason for this is not one of empirical optimization. Such stepwise dilution is important in that the total amount of combined CEA and CEA-like molecules recovered in the filtrate far exceeds the capacity of currently available assay kits.

The method is preferably carried out without pretreatment of subject's bowel prior to obtaining of the sample, as such pretreatment can affect the CEA produced in the bowels. Phosphate buffered saline (pH 7.2) is preferably used as the diluent in the method of the invention. This diluent will decrease denaturation of CEA and CEA-like molecules which could occur with the use of other diluents.

In preferred embodiments, the method employs between about 0.5 and 5 grams of stool sample; and the detecting step is carried out using an immunometric assay, e.g., a radioimmunoassay, or an enzyme-linked-immunoassay.

The invention can be carried out using a dipstick coated with the anti-CEA monoclonal antibody, which is dipped sequentially, first in the filtered liquid mixture and after washing off unreacted and unwanted molecules in the buffer solution, next into a secondary CEA-specific enzyme labelled reagent, and after once more washing off, into a color developing solution, the appearance of color on the dipstick being indicative of the total concentration of CEA and/or CEA-like molecules in the original stool sample.

The present method of detecting stool CEA and CEA-like antigens offers the following additional advantages:

a) The use of random, freshly obtained stool avoids the need for diet restriction, cathartics, or enemas.
b) The buffered solution is devoid of any preservatives such phenols and the like, or sodium azide unless the sample obtained is to be meant for assay at a later time (longer than one hour) while being preserved at temperatures of $-20°$ C. to minimize bacterial growth.
c) There is no need for high precision filtration requiring the use of micropore filters of specific porosity, because filtration involves only separating gelatinous and coarse contaminants.
d) Centrifugation, dialysis, periodic acid and heat treatment are not necessary as these steps can affect the physicochemical nature of the antigen molecules and interfere with the highly sensitive RIA or ELISA assays.

In addition, the method of the present inventions does not require, characterization, high precision extraction, and purification of cancer specific CEA molecules. It provides, furthermore, a quantitative determination of randomly obtained stool CEA and CEA-like antigen contents, as a screening test for any pathologic condition of the large bowel which results in CEA or CEA-like antigens being secreted or discharged into bowel lumen over and above what might be present normally.

Other features and advantages of the invention will be apparent from the following detailed description thereof, and from the claims.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and material are now described. And unless mentioned otherwise, the techniques employed or contemplated herein are standard methodologies well known to one of ordinary skill in the art. The materials, methods and examples are illustrative only and not limiting.

The preferred embodiment of the method for determining CEA and CEA-like antigens in stool samples is now described, and includes the following steps:

1. A fresh stool sample, about 0.5 to 5 grams, formed or liquid, is randomly obtained in a dry and clean receptacle without any prior chemical or physical preparation of the bowels.

2. The stool specimen is thoroughly stirred with a glass rod to ensure uniform mixing of any CEA and CEA-like antigen which might have come into contact with only a part of the surface of the feces. Liquid stool is shaken in a clean glass or plastic container for the same purpose.

3. A one-gram specimen of the above homogenized stool, whether formed or liquid, is placed in a separate clean dry glass beaker.

4. A phosphate buffered saline solution (PBS pH 7.21) and 0.15 molarity is prepared by dissolving about 20 grams of NaCl, 0.5 grams of KCl and 14.3 milliliters of a solution of Na2HPO4 and 0.5 grams of KH2PO4, in 1000 ml of distilled water.

5. Twenty five milliliters of this PBS pH 7.2 solution are poured into the beaker of step 3 containing one gram of the stool homogenate and thoroughly mixed to allow thorough dissolution of the stool sample in the buffered solution. (Lesser amount of fecal matter could be incorporated into this step of the procedure if proportionality of 1:25 w/v of stool to buffer solution is preserved.)

6. All of the stool specimen dissolved in the buffered solution is passed through a commercially available ashless general purpose gravimetric filter paper with medium speed and retention designed for retention of coarse and gelatinous particles (for example: "Whatman #40" filter paper, Catalog No. 1440 125, not to be mistaken for the very fine "Grade 40" Quantitative filter paper of 8 $\mu$m particle retention size, Catalog No. 1440 Y 125 as indicated in Whatman Price List of Jan. 1st, 1989).

7. The filtrate is either used for assay or stored at $-20°$ C. until ready to be used for assay.

8. For radioimmunoassay (RIA) of CEA and CEA-like antigens, the filtrate is first brought to room temperature (about $22°$–$24°$ C.) and diluted 1:1000, volume to volume, with the above-mentioned PBS pH 7.2 solution.

9. 50 $\mu$l of the diluted filtrate are then utilized in a two-site radioimmunometric assay (sandwich principle) based on the use of commercially available monoclonal antibodies having specific binding affinity for CEA (such as available from Byk-Sangtec Co. Diagnostica, D-6057 Dietzenbach 2, Germany). The CEA and CEA-like moiety of the filtrate will interact with the anti-CEA monoclonal antibody coated on a suitable support such as polystyrene beads, tubes, microliter plates or the like. Free or unreacted non-specific CEA is then washed away while specifically reacted portion is determined by an 125 I-conjugated moiety, according to standard methods. Final CEA and CEA-like concentration in the filtrate is then calculated from the CPM obtained for the 50 $\mu$l sample in the assay.

10. As an alternative to step 9, 50 $\mu$l of the diluted filtrate is incorporated in a two-site standard ELISA (enzyme linked immunosorbent assay) system using the antibodies mentioned above for RIA and the final concentration obtained through optical absorbance at 405 or 492 nanometers. Other conventional immunoassay formats can be used as well.

11. Final concentration of CEA and CEA-like antigens in the stool is calculated by correcting for dilution factors employed in steps 5 and 8 and the results expressed in nanograms of CEA and CEA-like antigens per one gram stool:

$$CEA_s = D_1 \times D_2 \times CEA_f$$

where:
$CEA_s$ = CEA and CEA like antigens in stool in nanograms per gram stool
$CEA_f$ = CEA and CEA like antigens in filtrate in nanograms $D_1 = 25$ ml PBS pH 7.2 ⎫ amount adjusted to
$D_2 = 1000$ ml PBS pH 7.2 ⎭ measuring capacity of kit used

DIP Test for CEA and CEA-Like Antigens Detection

In accordance with the present invention a simple 'dip test' for home or office use is provided to detect different ranges of CEA and CEA-like antigens in stood specimens.

The dip test employs a solid support such as nitrocellulose film in the shape of a dip stick and the like, coated with a commercially available CEA-specific monoclonal antibody. This monoclonal antibody-coated solid support is dipped in a sample of the filtrate of step (7) described herein above and washed in the previously described buffer to remove unwanted and unreacted material. The same dipstick is entered into a solution of secondary antibody which is enzyme labelled (conjugated anti-CEA antibody) to react with the previously formed antigen-antibody complex. After washing the dipstick once more the the buffer solution to remove unbound conjugated antibodies, it is entered into an appropriate liquid developer for enzyme conjugate (such as beta galactosidase), which allows formation of various intensities of color development directly proportional to the original CEA and CEA-like antigens in the stool.

It is understood that the examples and embodiments described herein are for illustrative purposes only and that various modifications or changes in light thereof will be suggested to persons skilled in the art and are to be included within the spirit and purview of the application and scope of the amended claims.

EXAMPLE

Results of Colorectal Cancer Screening by Measuring Fecal CEA

I. Patients with histologically proven adenocarcinoma of colon and rectum
Number of patients: 48 (M: 33; F: 15).
Age: mean: 52 (range 19–90).

| Stool CEA (ng/gm stool): | |
|---|---|
| Mean concentration | 298,000 |
| Minimum concentration: | 11,000 |
| Maximum concentration: | 2,000,000 |

Percent Positivity: (42 patients with level of >25,000 ng/gm stool ): 87.5%.

| Serum CEA (ng/ml): | |
|---|---|
| Mean | 11.25 |
| Minimum | 0.1 |
| Maximum | 70.0 |

Percent Positivity: (14 patients with level of >5.0 ng/ml): 29.1%

II. Patients with no colorectal pathology on colonoscopy
Number of patients: 16 (M: 12; F: 4).
Age: mean 38 (range 32–72).

| Stool CEA (ng/gm stool): | |
|---|---|
| Mean concentration | 8,750 |
| Minimum concentration: | (undetectable) |
| Maximum concentration: | 57,500 |

Percent Positivity: (1 patient with levels >25,000 ng/gm stool): 6.25%

| Serum CEA (ng/ml): | |
|---|---|
| Mean | 2.6 |
| Minimum | 0.1 |
| Maximum | 8.23 |

Percent Positivity: (1 patient with level >5.0 ng/ml): 6.25%

III. Patients with "inflammatory condition" of large bowel
Ulcerative colitis:15, Crohn's Disease:3, Nonspecific colitis:1
Number of patients: 19 (M: 10; F: 9).
Age: mean 40 (range 26–65).

| Stool CRA (ng/gm stool): | |
|---|---|
| Mean concentration | 153,000 |
| Minimum concentration: | (undetectable) |
| Maximum concentration: | 762,500 |
| Serum CEA (ng/ml): | |
| Mean | 2.7 |
| Minimum | 0.1 |
| Maximum | 12.2 |

What is claimed is:

1. A method for detecting in a stool sample without centrifugation, comprising the steps of:
   a) mixing said stool sample with an aqueous buffer to yield a liquid mixture;
   b) filtering said liquid mixture through an ashless filter paper to remove coarse and gelatinous particles but not CEA and; and
   c) measuring CEA and in said filtered mixture.

2. The method of claim 1 wherein molecules smaller than 500,000 M.W. are not removed.

3. The method of claim 2 wherein said ashless filter paper has an average pore size of a "#40 Whatman" filter paper.

4. The method of claim 1 wherein said aqueous buffer is phosphate buffered saline.

5. The method of claim 1 wherein step (a) employs between about 0.5 and 5 g of stool sample.

6. The method of claim 5 wherein said stool sample and said aqueous buffer are mixed in a ratio of about one gram stool per twenty-five ml of aqueous buffer (1:25 w/v).

7. The method of claim 1 wherein step (a) employs a dilution of stool in buffered solution in the ratio of about one to twenty-five.

8. The method of claim 1 wherein the filtered liquid mixture is diluted to one to one thousand, v/v.

9. The method of claim 1 wherein the filtered liquid mixture is diluted at least one hundred fold, v/v. prior to detecting said carcinoembryonic antigens.

10. The method of claim 9 wherein the filtered liquid mixture is diluted at about 1:100–1:1,500.

11. The method of claim 10 wherein the filtered liquid mixture is diluted at about 1:100–1:1,200.

12. The method of claim 11 wherein the filtered liquid mixture is diluted at about 1:1,000.

13. The method of claim 1 wherein said detecting step is carried out using an immunometric assay.

14. The method of claim 13, wherein said immunometric assay is a radioimmunoassay.

15. The method of claim 13 wherein said immunometric assay is an enzyme-linked immunoassay.

* * * * *

UNITED STATES PATENT AND TRADEMARK OFFICE
CERTIFICATE OF CORRECTION

PATENT NO. : 5,380,647
DATED : January 10, 1995
INVENTOR(S) : Kamal Bahar

It is certified that error appears in the above-identified patent and that said Letters Patent is hereby corrected as shown below:

Col. 1, line 65, replace "preparing stood" with --preparing stool--;

Col. 5, line 10, replace "in stood specimens" with --in stool specimens--;

Col. 6, claim 1, line 31, replace "A method for detecting in a stool sample..." with --A method for detecting CEA in a stool sample...--.

Signed and Sealed this

Fifteenth Day of June, 1999

Attest:

Q. TODD DICKINSON

Attesting Officer   Acting Commissioner of Patents and Trademarks